United States Patent
Belz et al.

(10) Patent No.: US 10,179,184 B2
(45) Date of Patent: Jan. 15, 2019

(54) DEVICE FOR DISPENSING A FRAGRANCE, AND MOTOR VEHICLE HAVING SUCH A DEVICE

(71) Applicant: AUDI AG, Ingolstadt (DE)

(72) Inventors: Karsten Belz, Ingolstadt (DE); Georg Techel, Dresden (DE); Michael Holzer, Manching (DE)

(73) Assignee: AUDI AG, Ingolstadt (DE)

( * ) Notice: Subject to any disclaimer, the term of this patent is extended or adjusted under 35 U.S.C. 154(b) by 353 days.

(21) Appl. No.: 15/110,627

(22) PCT Filed: Nov. 25, 2014

(86) PCT No.: PCT/EP2014/003143
§ 371 (c)(1),
(2) Date: Jul. 8, 2016

(87) PCT Pub. No.: WO2015/104037
PCT Pub. Date: Jul. 16, 2015

(65) Prior Publication Data
US 2016/0325001 A1    Nov. 10, 2016

(30) Foreign Application Priority Data
Jan. 10, 2014   (DE) .................. 10 2014 000 313

(51) Int. Cl.
*A61L 9/03* (2006.01)
*B60H 3/00* (2006.01)
*A61H 33/12* (2006.01)

(52) U.S. Cl.
CPC .............. *A61L 9/03* (2013.01); *B60H 3/0021* (2013.01); *A61L 2209/111* (2013.01);
(Continued)

(58) Field of Classification Search
None
See application file for complete search history.

(56) References Cited

U.S. PATENT DOCUMENTS 3,806,701 A * 4/1974 Scott .................... A47J 27/004
                                                                  219/386
3,854,454 A * 12/1974 Lazaridis .................. F24H 1/20
                                                                  122/33

(Continued)

FOREIGN PATENT DOCUMENTS

DE    203 02 097 U1    8/2003
DE    103 05 481 A1    8/2004
(Continued)

OTHER PUBLICATIONS

International Search Report issued by the European Patent Office in International Application PCT/EP2014/003143.
(Continued)

*Primary Examiner* — Thor S Campbell
(74) *Attorney, Agent, or Firm* — Henry M. Feiereisen LLC

(57) ABSTRACT

A device for dispensing a fragrance includes a container which has at least one outlet opening and is used for receiving the fragrance. Associated to the container is an electric heating element for heating the fragrance and a temperature sensor for detecting the temperature of the fragrance. The electrical heating element is controlled by a controller as a function of the temperature detected by the temperature sensor.

13 Claims, 1 Drawing Sheet

(52) U.S. Cl.
CPC ..... *A61L 2209/135* (2013.01); *A61L 2209/16* (2013.01); *B60H 2003/005* (2013.01)

(56) References Cited

U.S. PATENT DOCUMENTS

| | | | | |
|---|---|---|---|---|
| 5,031,229 | A | * | 7/1991 | Chow .................. C23C 14/243 |
| | | | | 392/389 |
| 5,175,791 | A | * | 12/1992 | Muderlak ................ A61L 9/03 |
| | | | | 219/492 |
| 5,432,882 | A | | 7/1995 | Glynn |
| 5,574,821 | A | * | 11/1996 | Babasade ................ A61L 9/03 |
| | | | | 392/390 |
| 5,644,866 | A | * | 7/1997 | Katsuda ............. A01M 1/2077 |
| | | | | 238/56 |
| 5,921,314 | A | | 7/1999 | Schuller et al. |
| 5,937,141 | A | * | 8/1999 | Swiatosz ................. F41H 9/06 |
| | | | | 392/397 |
| 6,169,852 | B1 | * | 1/2001 | Liao ....................... F22B 1/284 |
| | | | | 261/142 |
| 6,443,434 | B1 | * | 9/2002 | Prather .............. A01M 31/008 |
| | | | | 261/142 |
| 6,603,924 | B2 | * | 8/2003 | Brown ................ A01M 1/2077 |
| | | | | 219/541 |
| 6,783,117 | B2 | * | 8/2004 | Wohrle .................. A61L 9/035 |
| | | | | 261/104 |
| 7,223,166 | B1 | * | 5/2007 | Wiseman, Sr. ........... A61L 9/14 |
| | | | | 222/647 |
| 7,259,358 | B2 | * | 8/2007 | Mariner ............ H01L 21/67103 |
| | | | | 219/444.1 |
| 7,263,282 | B2 | * | 8/2007 | Meyer ................ A01M 1/2077 |
| | | | | 392/386 |
| 7,544,331 | B1 | * | 6/2009 | Pettaway .................. A61L 9/03 |
| | | | | 392/386 |
| 7,741,584 | B2 | * | 6/2010 | Mariner ................... H05B 3/24 |
| | | | | 219/444.1 |
| 8,170,405 | B2 | * | 5/2012 | Harris ................. A01M 1/2033 |
| | | | | 392/386 |
| 8,873,941 | B2 | * | 10/2014 | Row ................ A61M 16/1075 |
| | | | | 392/386 |
| 9,031,392 | B2 | * | 5/2015 | Hsiao .................. B60H 3/0007 |
| | | | | 392/386 |
| 2004/0007787 | A1 | | 1/2004 | Kvietok et al. |
| 2008/0085103 | A1 | * | 4/2008 | Beland .................... A61L 9/035 |
| | | | | 392/390 |
| 2009/0035188 | A1 | | 2/2009 | Huang et al. |

FOREIGN PATENT DOCUMENTS

| | | |
|---|---|---|
| DE | 10 2005 025 755 A1 | 1/2006 |
| DE | 20 2005 019 989 U1 | 8/2006 |
| WO | WO 03/019082 | 3/2003 |
| WO | WO 03/019082 A1 | 3/2003 |
| WO | WO 2006/057550 | 6/2006 |
| WO | WO 2013/111842 | 8/2013 |
| WO | WO 2013/111842 A1 | 8/2013 |

OTHER PUBLICATIONS

Chinese Search Report dated May 2, 2017 with respect to counterpart Chinese patent application 201480070515.7.
Translation of Chinese Search Report dated May 2, 2017 with respect to counterpart Chinese patent application 201480070515.7.

* cited by examiner

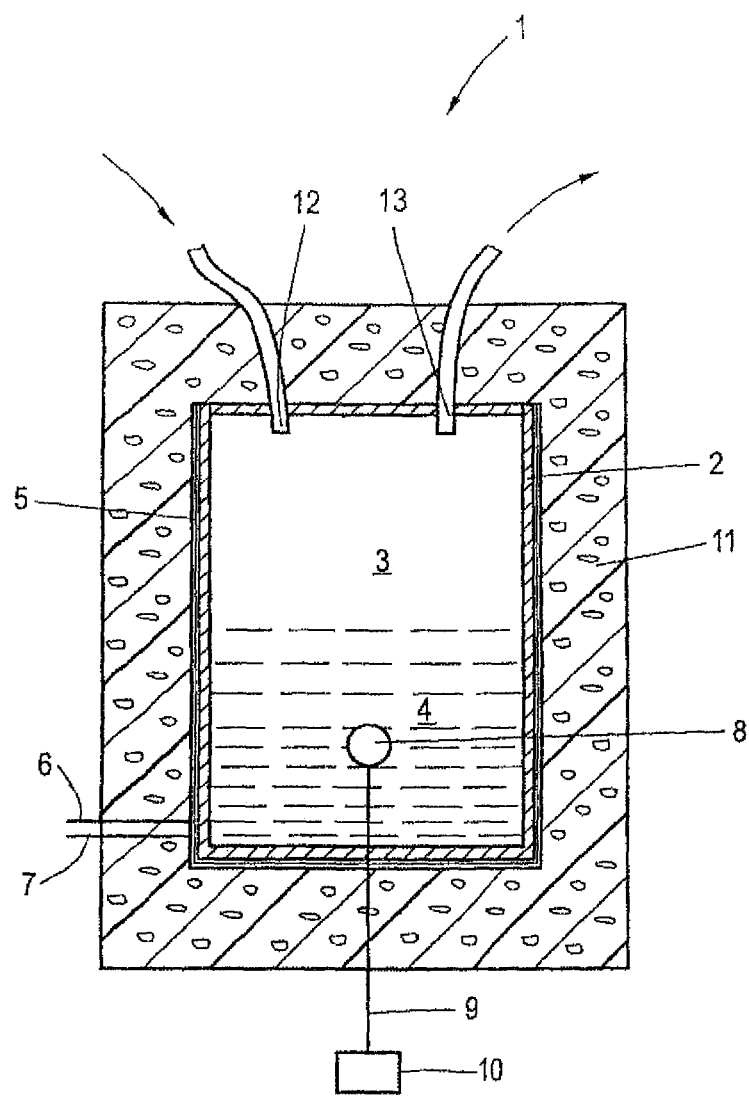

DEVICE FOR DISPENSING A FRAGRANCE, AND MOTOR VEHICLE HAVING SUCH A DEVICE

CROSS-REFERENCES TO RELATED APPLICATIONS

This application is the U.S. National Stage of International Application No. PCT/EP2014/003143, filed Nov. 25, 2014, which designated the United States and has been published as International Publication No. WO 2015/104037 and which claims the priority of German Patent Application, Serial No. 10 2014 000 313.2, filed Jan. 10, 2014, pursuant to 35 U.S.C. 119(a)-(d).

BACKGROUND OF THE INVENTION

The invention relates to a device for dispensing a fragrance, including a container, having at least one outlet opening, for receiving the fragrance, and an electric heating element, associated to the container, for heating of the fragrance.

Various fragrance dispensers have already been proposed to automatically dispense a fragrance.

DE 103 05 481 A1 proposes a fragrance or perfume dispenser, which has a motion sensor. When detecting a person in the surrounding area of the fragrance dispenser, a fragrance is sprayed or heated by a heating element and dispersed in the air. Optionally, provision may also be made for a blower. This fragrance dispenser may include a plug for a cigarette lighter socket, so that it can be operated in a vehicle.

Document DE 20 2005 019 989 U1 discloses a room scent unit with an evaporation body having a heating unit. The fragrance is dispersed by a fan.

DE 10 2005 025 755 A1 discloses a device for dispersing aromatic substances in an interior space of a motor vehicle. The device includes a housing for receiving the fragrance, wherein the housing can be selectively opened or closed by at least one actuatable opening. By cyclically actuating the movable opening, the vehicle can be scented with controlled doses of fragrances.

Document DE 203 02 097 A1 discloses a scent dispenser for the interior space of a vehicle, including a power connection which is appropriate for the on-board power supply of a vehicle. The scent dispenser includes an electrical heating element which heats a container, filled with scent material, slowly or quickly and releases the fragrance.

Release of a precise dosage of fragrances into the relatively small interior of a motor vehicle is of high importance. When the dosage is too low, the fragrance is not perceived at all or not to a sufficient extent. Conversely, a dosage that is too high is perceived by passengers as unpleasant or bothersome.

SUMMARY OF THE INVENTION

The invention is therefore based on the object to provide a device for dispensing a fragrance that enables release of a precise dosage.

This object is attained in a device of the afore-mentioned type by providing in accordance with the invention a temperature sensor, which is associated to the container, for detecting the temperature of the fragrance, and a controller for controlling the electrical heating element as a function of the detected temperature.

The invention is based on the recognition that the provision of a heating element by itself is inadequate to effect a precise dosage of the fragrance. The reason for this is that the perception of fragrances is greatly temperature-dependent. In the presence of cold outside temperatures, for example below the freezing point, the olfactory perception of many fragrances or their components is barely noticeable. Conversely, the majority of scents can easily be smelled at about 20° C. At higher temperatures, the components of the fragrance evaporate faster. Fragrances are comprised of a variety of different high-volatile to low-volatile fractions, so that a reproducible scent impression can only be achieved at comparable temperatures. For that reason, the electric heating element of the device according to the invention is heated to a predefined, constant temperature by the controller.

The device according to the invention can be implemented in a particularly easy manner, when the heating element is configured as a film which is disposed on at least an inner surface of the container. According to a refinement of the invention, the film itself may be formed as a container. The film includes one or more electrically conductive conductor paths which are heated when applying a voltage.

In order to reduce power consumption, provision may be made in the device according to the invention for the container to include a heat insulation layer which at least partially surrounds the container. Preferably, the heat insulation layer may be made of foamed plastic, as an alternative, a different material having low thermal conductivity can be used. For example, the heat insulation layer may be formed as a hollow body, which provides thermal insulation of the container disposed in the hollow body. It is also possible that the heat insulation layer itself, configured as hollow body, forms the container.

According to a refinement of the invention, the controller is configured to heat the fragrance to a temperature between 10° C. and 30° C., in particular to approximately 20° C. By heating to a substantially constant temperature range, in particular to 20° C., a reproducible scent impression can be created.

It is conceivable that the device according to the invention, in particular its container, has an air access opening. This air access opening enables incoming air to sweep over the surface of the liquid fragrance and to exit the device via the outlet opening.

In addition, the invention relates to a motor vehicle including a device of the type described.

In the motor vehicle according to the invention, it is preferred to connect the electric heating element of the device to the on-board electrical system of the motor vehicle.

It is particularly beneficial, when coupling the device of the vehicle according to the invention to a ventilation and/or air conditioning system of the motor vehicle such that the fragrance arranged in the container can be exposed to an air flow. The air flow flows through the container of the device, so that the fragrance evaporates and is dispersed in the interior space of the motor vehicle.

BRIEF DESCRIPTION OF THE DRAWING

An exemplary embodiment of the invention will become apparent hereinafter with reference to the drawing, in which the sole FIG. 1 shows a schematic sectional view of a device according to the invention for dispensing a fragrance for use in a motor vehicle.

DETAILED DESCRIPTION OF PREFERRED EMBODIMENTS

The device 1 shown in the drawing includes a container 2, which is formed in the illustrated exemplary embodiment as a hollow cylinder. A hollow space 3 inside the container 2 is filled with a liquid fragrance 4. For temperature control of the fragrance 4, the container 2 is provided with a heating element 5 which is embodied as a film. Other embodiments are also possible in which the heating element is located on the inside of the container. The heating element 5 includes schematically illustrated electrical connection lines 6, 7, which are connected to the on-board electrical system of a motor vehicle. When applying a voltage on the connection lines 6, 7, the heating element 5 is heated. Arranged inside the container 2 is a temperature sensor 8, which can be located at any desired location. Preferred is the attachment of the temperature sensor 8 in the center of the container 2, or on the bottom, or on the sidewall. The temperature sensor 8 detects the temperature of the fragrance 4, with the temperature sensor 8 being connected via an electric line 9 to a controller 10. The controller 10 is provided to control the electric heating element. Control can be effected, for example, by controlling current flowing through the heating element 5; as an alternative, a constant current may be applied to the heating element, with the supply of current being carried out intermittently by the controller 10. In the illustrated exemplary embodiment, the controller 10 is configured to heat the fragrance 4 to a temperature of 20° C.

It is apparent from the drawing that the container 2 is surrounded by a heat insulation layer 11, which is provided for thermal insulation of the fragrance 4 and made of foamed plastic.

Provision is made at the top of the container 2 for an air access opening 12, and next to it an outlet opening 13 at the top of the container 2. The two openings are spaced from each other, they can also be arranged on opposite sides of the container 2.

The air access opening 12 includes a tube, via which the device 1 is connected to a ventilation and air conditioning system of the motor vehicle. The ventilation and air conditioning system generates an air flow which is fed via the tube and the air access opening 12 to the container 2, so that the surface of the liquid fragrance 4 is exposed to the air flow. As it evaporates, the heated fragrance 4 is picked up by the air flow and exits the device 1 via the outlet opening. 13

As a result of the temperature control of the fragrance 4, with the predefined temperature being the controlled variable, the scent impression is the same at all times, regardless of the outside temperature or the inside temperature of the motor vehicle.

The invention claimed is:

1. A device for dispensing a fragrance, comprising:
a container receiving the fragrance and having an outlet opening for discharge of the fragrance, said container including an air access opening comprising a tube configured to be connected to a ventilation and/or air conditioning system of a motor vehicle, wherein the ventilation and/or air conditioning system generates an air flow which is fed via the tube and the air access opening to the container so as to expose the fragrance in the container to an air flow;
an electric heating element operably connected to the container for heating the fragrance, said electrical heating element configured as a film having at least one conductor path which is heatable when applying a voltage, said film being arranged at least on an inner surface of the container;
a temperature sensor configured to detect a temperature of the fragrance in the container; and
a controller configured to control the electrical heating element as a function of the temperature detected by the temperature sensor.

2. The device of claim 1, further comprising a heat insulation layer configured to at least partially surround the container.

3. The device of claim 2, wherein the heat insulation layer is made of foamed plastic.

4. The device of claim 1, wherein the controller is configured to heat the fragrance to a temperature between 10° C. and 30° C.

5. The device of claim 1, wherein the controller is configured to heat the fragrance to a temperature of approximately 20° C.

6. A motor vehicle, comprising a device for dispensing a fragrance, said device comprising:
a container receiving the fragrance and having an outlet opening for discharge of the fragrance, said container including an air access opening comprising a tube configured to be connected to a ventilation and/or air conditioning system of the motor vehicle, wherein the ventilation and/or air conditioning system generates an air flow which is fed via the tube and the air access opening to the container so as to expose the fragrance in the container to an air flow,
an electric heating element operably connected to the container for heating the fragrance, said electrical heating element configured as a film having at least one conductor path which is heatable when applying a voltage, said film being arranged at least on an inner surface of the container,
a temperature sensor configured to detect a temperature of the fragrance in the container, and
a controller configured to control the electrical heating element as a function of the temperature detected by the temperature sensor.

7. The motor vehicle of claim 6, wherein the device comprises a heat insulation layer configured to at least partially surround the container.

8. The motor vehicle of claim 7, wherein the heat insulation layer is made of foamed plastic.

9. The motor vehicle of claim 6, wherein the controller is configured to heat the fragrance to a temperature between 10° C. and 30° C.

10. The motor vehicle of claim 6, wherein the controller is configured to heat the fragrance to a temperature of approximately 20° C.

11. The motor vehicle of claim 6, further comprising an on-board electrical system, said electrical heating element of the device being connected to the on-board electrical system of the motor vehicle.

12. The motor vehicle of claim 6, wherein the air access opening is located at a distance to the outlet opening, said access opening configured to allow the air flow to enter the container and pick up the fragrance as it evaporates, for discharge through the outlet opening.

13. The motor vehicle of claim 12, wherein the air access opening and the outlet opening are arranged on a topside of the container.

* * * * *